(12) United States Patent
Nativ et al.

(10) Patent No.: US 10,918,388 B2
(45) Date of Patent: Feb. 16, 2021

(54) ANASTOMOTIC STAPLING REINFORCING BUTTRESS AND METHODS OF DEPLOYMENT

(71) Applicant: Ethicon, Inc., Somerville, NJ (US)

(72) Inventors: Nir I. Nativ, West Orange, NJ (US);
Yufu Li, Bridgewater, NJ (US);
Michael Logue, New Hope, PA (US);
Glenn Cook, Clinton, NJ (US);
Gwan-Ywan Lai, Princeton Junction, NJ (US)

(73) Assignee: Ethicon, Inc., Somerville, NJ (US)

( * ) Notice: Subject to any disclaimer, the term of this patent is extended or adjusted under 35 U.S.C. 154(b) by 198 days.

(21) Appl. No.: 16/110,388

(22) Filed: Aug. 23, 2018

(65) Prior Publication Data
US 2019/0008519 A1    Jan. 10, 2019

Related U.S. Application Data

(62) Division of application No. 15/088,455, filed on Apr. 1, 2016, now abandoned.

(51) Int. Cl.
| | | |
|---|---|---|
| *A61B 17/115* | (2006.01) | |
| *A61B 17/072* | (2006.01) | |
| *A61B 17/064* | (2006.01) | |
| *A61B 17/11* | (2006.01) | |
| *A61B 17/00* | (2006.01) | |
| *A61B 17/04* | (2006.01) | |

(52) U.S. Cl.
CPC ...... *A61B 17/1155* (2013.01); *A61B 17/0644* (2013.01); *A61B 17/072* (2013.01); *A61B 17/07292* (2013.01); *A61B 17/115* (2013.01); *A61B 17/1114* (2013.01); *A61B 2017/00477* (2013.01); *A61B 2017/0406* (2013.01); *A61B 2017/1132* (2013.01)

(58) Field of Classification Search
CPC ............. A61B 17/1155; A61B 17/1114; A61B 17/0644; A61B 17/115; A61B 17/07292; A61B 17/072; A61B 2017/1132; A61B 2017/0406; A61B 2017/00477
See application file for complete search history.

(56) References Cited

U.S. PATENT DOCUMENTS

| | | |
|---|---|---|
| 5,271,544 A | 12/1993 | Fox et al. |
| 7,547,312 B2 | 6/2009 | Bauman et al. |

(Continued)

FOREIGN PATENT DOCUMENTS

| | | |
|---|---|---|
| EP | 2604195 | 6/2013 |

OTHER PUBLICATIONS

International Search Report re: PCT/US2017/024467 dated Jun. 6, 2017.
Written Opinion re: PCT/US2017/024467 dated Jun. 6, 2017.

*Primary Examiner* — Julian W Woo
(74) *Attorney, Agent, or Firm* — David R. Crichton; Leo B. Kriksunov

(57) ABSTRACT

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections so as to improve tissue viability, prevent tissue infection, and to prevent leakage.

3 Claims, 16 Drawing Sheets

(56) References Cited

U.S. PATENT DOCUMENTS

| | | | |
|---|---|---|---|
| 7,776,060 B2 | 8/2010 | Mooradian et al. | |
| 7,938,307 B2* | 5/2011 | Bettuchi | A61B 17/115 227/179.1 |
| 8,123,766 B2 | 2/2012 | Bauman et al. | |
| 8,123,767 B2 | 2/2012 | Bauman et al. | |
| 8,167,895 B2 | 5/2012 | D'Agostino et al. | |
| 8,215,533 B2* | 7/2012 | Viola | A61B 17/072 227/175.1 |
| 8,430,291 B2* | 4/2013 | Heinrich | A61B 17/00491 227/179.1 |
| 8,529,819 B2 | 9/2013 | Ostapoff et al. | |
| 8,657,176 B2* | 2/2014 | Shelton, IV | A61B 17/00491 227/178.1 |
| 8,679,137 B2 | 3/2014 | Bauman et al. | |
| 9,005,243 B2 | 4/2015 | Stopek et al. | |
| 9,010,609 B2 | 4/2015 | Carter et al. | |
| 9,010,612 B2 | 4/2015 | Stevenson et al. | |
| 9,113,885 B2 | 8/2015 | Hodgkinson et al. | |
| 9,161,753 B2 | 10/2015 | Prior | |
| 9,186,144 B2 | 11/2015 | Stevenson et al. | |
| 9,554,802 B2* | 1/2017 | Williams | A61B 17/1155 |
| 9,775,618 B2* | 10/2017 | Bettuchi | A61B 17/07207 |
| 10,117,649 B2* | 11/2018 | Baxter, III | A61B 17/072 |
| 10,154,840 B2* | 12/2018 | Viola | A61B 17/00491 |
| 10,285,704 B2* | 5/2019 | Prior | A61B 17/068 |
| 10,357,249 B2* | 7/2019 | Carter | A61B 17/105 |
| 10,390,827 B2* | 8/2019 | Hodgkinson | A61F 2/0063 |
| 10,499,913 B2* | 12/2019 | Vendely | A61M 37/00 |
| 2005/0059996 A1 | 3/2005 | Bauman et al. | |
| 2005/0059997 A1 | 3/2005 | Bauman et al. | |
| 2010/0012703 A1* | 1/2010 | Calabrese | C08G 18/6674 227/176.1 |
| 2013/0123816 A1 | 5/2013 | Hodgkinson et al. | |
| 2014/0197224 A1 | 7/2014 | Penna | |
| 2014/0217148 A1 | 8/2014 | Penna | |

* cited by examiner

ANASTOMOTIC STAPLING REINFORCING BUTTRESS AND METHODS OF DEPLOYMENT

This application is a divisional application of co-pending U.S. application Ser. No. 15/088,455 filed on Apr. 1, 2016, the complete disclosure of which is hereby incorporated herein by reference for all purposes.

FIELD OF THE INVENTION

The present invention relates to surgical instruments and methods for enhancing properties of tissue repaired or joined by surgical staples and, more particularly to surgical instruments and methods designed to reinforce the repaired or adjoined tissue at a target surgical site.

BACKGROUND OF THE INVENTION

Throughout the years the medical field has utilized various techniques in an effort to join or bond body tissue together. Historically, suturing was the accepted technique for rejoining severed tissues and closing wounds. Suturing is achieved with a surgical needle and a suturing thread, with the intended function of sutures to hold the edges of a wound or tissue against one another during the healing process. Staples are used to replace suturing when joining or anastomosing various body structures, such as, for example, the bowel. The surgical stapling devices employed to apply staples are generally designed to simultaneously cut and seal an extended segment of tissue in a patient.

Linear or annular/circular surgical stapling devices are employed by surgeons to sequentially or simultaneously apply one or more rows of surgical fasteners, e.g., staples, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated, firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular or circular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

Anastomotic leaks may result in significant morbidity and frequently death. In addition to the use of surgical staples, sealants, e.g., synthetic or biological sealants, can be applied to the surgical site to guard against leakage. The biological sealants are typically applied to the outer surface of the anastomosis in a separate step.

U.S. Pat. No. 7,547,312 which is directed to circular stapler buttress discloses an implantable medical device adapted to reinforce a surgical opening formed in a patient with a circular stapler having a cutting blade, said device comprising: a buttress material adapted for mounting on said circular stapler, said stapler having an anvil that is larger in diameter than said surgical opening that is created by said cutting blade, wherein following stapling with said stapler and cutting with said cutting blade, said buttress material is adapted to reinforce stapled tissue surrounding said surgical opening created by said cutting blade in said patient and has an adaptive opening formed therein; wherein the buttress material comprises a bioabsorbable web material substantially in the form of a circle, said circular web material having an outer edge and a centrally located opening delimiting an inner edge; at least two disruptable areas positioned along said outer edge of said circular web material and at least two protrusions of web material each extending beyond each of said at least two disruptable areas, wherein said protrusions are adapted to attach said buttress material to said circular stapler; a series of slits in said bioabsorbable web material positioned between said outer edge and said inner edge of said circular web material; wherein said series of slits serve to create said adaptive opening in said buttress material; wherein said adaptive opening corresponds to said surgical opening in said patient and has a diameter smaller than said diameter of said anvil; and wherein said adaptive opening allows said anvil to be removed therethrough without causing permanent alteration to said buttress material.

U.S. Pat. No. 8,123,767 which is directed to a circular stapler buttress discloses an implantable medical device for use with a circular stapler adapted to create a substantially circular hole in a patient, said circular stapler having a stapler anvil portion with a first compression surface and a stapler body portion with a second compression surface, said implantable medical device comprising: a first buttress made of a bioabsorbable web material having a first contact surface adapted to attach to said stapler anvil without use of an adhesive on said first compression surface and said first contact surface; a second buttress made of a bioabsorbable web material having a second contact surface adapted to attach to said stapler body without use of an adhesive on said second compression surface and said second contact surface; at least one protrusion disruptably connected to said second buttress, said protrusion having an adhesive on at least a portion thereof to attach said second buttress to said stapler body portion; and wherein the first and second buttresses reinforce said hole created by said stapler in said patient when staples are applied and both have an adaptive opening therethrough formed from a series of slits positioned between inner and outer edges of the first and second buttresses.

U.S. Pat. No. 8,123,766 which is directed to a circular stapler buttress discloses an implantable medical device adapted to reinforce tissue stapled together with a circular stapler having a generally circular cutting blade, the device comprising: a buttress material adapted for mounting on the circular stapler; and a plurality of slits in the buttress material, the slits generally extending in an approximately radial direction, wherein, a reinforcing portion of the buttress material is configured to remain stapled to tissue in a patient and an inner portion of the buttress material is configured to be cut away from the reinforcing portion by the cutting blade upon actuation of the circular stapler and cutting blade, resulting in a severed inner edge of the reinforcing portion and a severed outer edge of the inner portion, and wherein the slits extend through the severed inner edge of the reinforcing portion.

U.S. Pat. No. 8,679,137 which is directed to a circular stapler buttress discloses a medical device adapted to reinforce tissue stapled together with a circular surgical stapler having an anvil and a generally circular cutting blade, the medical device comprising: an implantable buttress material adapted for mounting on said circular stapler; and at least one adaptive opening in the buttress material wherein a reinforcing portion of the buttress material is configured to remain stapled to tissue in a patient and an inner portion of the buttress material is configured to be cut away from the reinforcing portion by the cutting blade upon actuation of the circular stapler and cutting blade, resulting in a severed inner edge of the reinforcing portion and a severed outer edge of the inner portion, and wherein the at least one adaptive opening is adapted to extend to a central opening in said buttress material created by cutting of said inner portion away from said reinforcing portion with said generally circular cutting blade.

U.S. Pat. No. 7,776,060 which is directed to a circular stapler buttress combination discloses a combination medical device comprising: a) a circular stapler instrument, comprising a staple cartridge component and corresponding anvil component, and b) a buttress adapted to be a) stably positioned upon the staple cartridge and/or anvil components of the stapler prior to, or at the time of, use, b) while in position upon the stapler component(s), to then be delivered to a tissue site in combination with the stapler components, c) upon delivery of the components and positioned buttress to the tissue site, to provide a first region of buttress material to buttress a seam between tissue sections upon activation of the stapler instrument, and d) to permit the removal of one or more portions of a second region upon activation of a stapler instrument knife provided by the stapler, the second region being generally concentric to the first region and wherein the first region and the second region are formed of dissimilar materials.

U.S. Pat. No. 8,529,819 which is directed to wound closure material discloses a method comprising: obtaining a polymeric material selected from the group consisting of glycolic acid, lactic acid, glycolide, lactide, dioxanone, trimethylene carbonate, caprolactone, and combinations thereof; forming the polymeric material into an article that does not possess orientation in a single direction by subjecting the polymeric material to a temperature of from about 95 C to about 230 C and a pressure of from about 1 psi to about 2500 psi, for a period of time from about 5 seconds to about 10 minutes; and recovering the article.

U.S. Pat. No. 9,161,753 which is directed to buttress fixation for a circular stapler discloses a circular stapling apparatus, comprising: an anvil assembly including an anvil member and a shaft; a tubular body portion having a staple cartridge including a plurality of staple receiving slots defined in a tissue contacting surface of the staple cartridge, each of the plurality of staple receiving slots including a staple disposed therein, and at least one of the plurality of staple receiving slots includes a notch, the shaft of the anvil assembly being connectable to the tubular body portion so that the anvil assembly is movable toward and away from the tubular body portion, the staple cartridge including a staple pusher disposed therein, the staple pusher having a plurality of fingers for driving the staples out of the plurality of staple receiving slots, at least one of the fingers including a protrusion; and a buttress material removably attached to the staple cartridge by at least one anchor releasably retained within the notch, the staple pusher being movable to move the protrusion into engagement with the anchor retained within the notch to push the anchor out from the notch.

U.S. Pat. No. 9,113,885 which is directed to buttress assembly for use with surgical stapling device discloses an apparatus for joining two hollow organ sections, the apparatus comprising: a staple cartridge component including a plurality of surgical staples in an annular array; an anvil component defining a plurality of staple pockets for deforming the plurality of surgical staples, the anvil component movable relative to the staple cartridge component between spaced apart and approximated positions to adjustably clamp tissue between the staple cartridge and anvil components; a knife member concentrically arranged with the plurality of surgical staples in the staple cartridge component, the knife member defining a lumen therethrough, the knife member movable relative to the staple cartridge component; and a buttress member including a pair of anchor portions securely engaging an inner wall of the staple cartridge component, the inner wall defining a passage dimensioned to receive the knife member therein, wherein each anchor portion of the pair of anchor portions is disposed radially inward of the inner wall of the staple cartridge component.

U.S. Pat. No. 9,186,144 which is directed to buttress support design for an anvil discloses an apparatus for joining two hollow organ sections with an annular array of surgical staples, the apparatus comprising: a staple cartridge component including a plurality of surgical staples in an annular array; an anvil component including an anvil member and a shaft extending therefrom, the anvil member defining a plurality of staple pockets for deforming the plurality of surgical staples, the anvil component movable relative to the staple cartridge component between spaced apart and approximated positions to adjustably clamp tissue between the staple cartridge and anvil component; a buttress member in registration with at least a portion of the plurality of staple pockets defined in the anvil member; and a buttress mount secured to the shaft of the anvil component, the buttress mount configured to be received in a recess defined in the anvil member, the buttress mount including at least one support member configured to engage a peripheral edge of the recess of the anvil member to secure the buttress mount within the recess, wherein the buttress mount is attached to a distal surface of the buttress member.

U.S. Pat. No. 9,010,612 which is directed to buttress support design for an anvil discloses an apparatus for joining two hollow organ sections with an annular array of surgical staples, the apparatus comprising: a staple cartridge component including a plurality of surgical staples in the annular array; an anvil component including an anvil member and a shaft extending therefrom, the anvil member defining a plurality of staple pockets for deforming the plurality of surgical staples, the anvil component movable relative to the staple cartridge component between spaced apart and approximated positions to adjustably clamp tissue between the staple cartridge and anvil components; a buttress member concentrically aligned with the plurality of staple pockets defined in the anvil member; and a buttress mount detachably secured with the shaft of the anvil component, the buttress mount including an annular ring member and at least one support member radially extending outward from the annular ring member to secure the buttress member to the anvil member, the at least one support member at least partially underlying the buttress member to provide support thereto, wherein the buttress mount is separate from the buttress member, and the annular ring member of the buttress mount is secured to the shaft of the anvil component.

U.S. Pat. No. 9,010,609 which is directed to a circular stapler including buttress discloses a surgical stapling device for joining tissue portions, comprising: a handle assembly; a tubular body portion supported on a distal end of the handle assembly, the tubular body portion having a staple cartridge assembly containing a plurality of surgical staples in an annular array, the tubular body portion including an inner surface and an outer surface, a distal portion of the tubular body portion including at least one attachment portion defining a first cleat; an anvil assembly at a distal end of the surgical stapling device, the anvil assembly having a shaft for removably connecting the anvil assembly to the tubular body portion, the anvil assembly and tubular body portion being juxtaposed with respect to one another along the shaft and arranged so as to be approximated with respect to one another; a buttress material supported by the tubular body portion, the buttress material being disposed between the anvil assembly and the staple cartridge assembly; and an attachment member adapted for engagement with the tubular body portion and the buttress material to secure the buttress material to the tubular body portion, the attachment member defining a first end and a second end, the attachment member being adapted to engage the tubular body portion by insertion of at least one of the first and second ends thereof into the first cleat of the at least one attachment portion.

U.S. Pat. No. 9,005,243 which is directed to a buttress and surgical stapling apparatus discloses a surgical stapling apparatus comprising: a staple cartridge containing at least one staple; an anvil having a staple forming surface; and a buttress positioned adjacent the anvil or the cartridge, the buttress comprising a non-porous layer disposed between first and second porous layers and a reinforcement member positioned within the non-porous layer, wherein pores of the porous layers do not span across the entire thickness of the porous layers.

U.S. Pat. No. 8,167,895 which is directed to an anastomosis composite gasket discloses a method of forming an anastomosis between intestinal tissue sections, comprising the steps of: providing a circular surgical anastomosis device, the circular surgical anastomosis device including: an anvil assembly having an anvil member; and a tubular body portion having an annular knife operatively disposed therein and a shaft disposed radially inward of the annular knife, the anvil assembly being attached to the shaft of the tubular body; inserting the anvil assembly into a first intestinal section; inserting the tubular body portion into a second intestinal section; disposing a structure, including at least a first ring of a first material, a second ring of a second material, and a third ring between the first intestinal section and the second intestinal section, the first ring comprising a disk having an aperture and the second ring comprising a disk having an aperture, the second ring having an outer perimeter, wherein the outer perimeter of the second ring is directly attached to the first ring and disposed within the aperture of the first ring, and the third ring radially extending outward from the first ring and beyond staple retaining slots of the tubular body portion, the structure possessing a wound treatment material consisting of at least one of an adhesive and a sealant; and firing staples through the intestinal tissue sections and through the structure.

U.S. Pat. No. 7,938,307 which is directed to support structures and methods of using the same discloses an apparatus for forming an anastomosis between adjacent intestinal sections of tissue, comprising: a) an anastomosis device having an anvil and a tubular body portion, the anvil being selectively attachable to the tubular body portion by a shaft; and b) a support structure for deposition between the intestinal sections of tissue, the support structure including a body defining an aperture therein for receiving the shaft, the body having an outer terminal edge, wherein the body is compressible so that the outer terminal edge of the body extends beyond the outer radial surface of the anvil and the tubular body portion, the support structure including at least one layer of expandable material disposed at the outer terminal edge of the body, wherein the support structure has an unhydrated condition wherein the body has a first diameter and a first thickness, and a hydrated condition wherein the body has a second diameter greater than the first diameter and a second thickness greater than the first thickness, and wherein the body expands from the first diameter and the first thickness to a second diameter and a second thickness upon application of a fluid thereto, the body being constructed from a first part of a two-part wound treatment material, and the fluid applied thereto is a second part of the two-part wound treatment material.

U.S. Patent Publication No. 2013/0123816 which is directed to hydrophilic medical devices discloses a method of making an absorbent surgical buttress, comprising: generating a plurality of fibers; collecting the plurality of fibers so that they adhere to one another and form a non-woven material; plasma treating at least a portion of a surface of the non-woven material with an ionizable gas species or combination of ionizable gas species configured to chemically modify or functionalize the surface of the non-woven material; and cutting the non-woven material into a desired shape for a surgical buttress.

U.S. Patent Publication No. 2005/0059997 which is directed to a circular stapler buttress discloses a reinforcement device for use with a circular stapler that is adapted to create and seal a surgical opening in a patient comprising: a buttress adapted for mounting on the circular stapler, the stapler having an anvil that is larger in diameter than the surgical opening that is created by the stapler, wherein following stapling with the stapler, the buttress reinforces the surgical opening created by the stapler in the patient; wherein the buttress includes at least one adaptive opening created by the circular stapler which corresponds to the surgical opening in the patient, said adaptive opening when circular having a diameter smaller than the diameter of the anvil, and wherein the adaptive opening in the buttress allows the anvil to be removed therethrough without causing permanent alteration to the buttress.

U.S. Patent Publication No. 2014/0217148 which is directed to a buttress attachment for circular stapling device discloses a circular stapling device, comprising: a handle assembly; an elongate body that extends from the handle assembly; a cartridge assembly mounted on a distal end portion of the elongate body, the cartridge assembly including: a housing; a pusher member supported within the housing and being movable between a first position and a second position; a retaining ring member supported on the housing and being configured and arranged to move between a radially constricted condition and a radially expanded condition in response to movement of the pusher member; and a fastener cartridge body supported on the housing and having a tissue engaging surface that extends to an annular edge; and a circular cartridge buttress member having a body portion and an extension portion, the body portion being supported on the tissue engaging surface of the fastener cartridge body, the extension portion extending from the body portion and over the annular edge of the tissue engaging surface, the retaining ring member securing the extension portion against at least one of the fastener cartridge body and the housing when in the radially constricted condition, the retaining ring member releasing the radially extension portion when the retaining ring member moves to the expanded condition in response to a movement of the pusher member from the first position to the second position so that the body portion of the cartridge buttress separates from the tissue engaging surface of the fastener cartridge body.

U.S. Patent Publication No. 2014/0197224 which is directed to a buttress retainer for an anvil discloses an apparatus for joining two hollow organ sections with an annular array of surgical staples, the apparatus comprising: a staple cartridge assembly including a plurality of surgical staples in an annular array; an anvil assembly including an anvil member and a shaft extending therefrom, the anvil member including a proximal surface defining a plurality of staple pockets for deforming the surgical staples, the anvil assembly movable relative to the staple cartridge assembly between spaced apart and approximated positions to adjustably clamp tissue between the staple cartridge and anvil assemblies; and a buttress assembly including: a ring member configured to engage a knife member, the ring member secured with the anvil member; a buttress member disposed in a superposed relation with the plurality of staple pockets defined in the anvil member; and a retaining member having an attaching member configured to be secured with the ring member to secure the buttress member between the cut ring and the retaining member, and to position the buttress member relative to the anvil assembly.

Post-operative leakage of the stapled tissue seals, including anastomotic seals has been shown to lead to morbidity and mortality. A number of technologies are related to direct application of material to the serosal layer after stapling by either dripping or spraying. The problems associated with these techniques are that access is very difficult and visual assessment as to whether or not the material was applied to the right spot and completely around the anastomosis. The material is also applied on top of the serosal layer when the target site is actually subserosal along the staple line. Applying a therapeutic agent to the serosal layer of the colon requires the material to migrate through the serosa and to the staple region, then provide a biological affect, and overcome the problems associated with a leak formation, all within 24-48 hours, and assuming the material was applied to the correct spot intraoperatively. One of the most challenging steps in the application of a topical adjunctive therapy to a colorectal anastomosis is to provide the material to the site because of the extreme limitation in access to the site. Some colorectal anastomoses are performed relatively "low" in a patient (i.e. lower anterior resection) and the actual staple line is deep within the pelvic canal, which makes a topical application of material around the circumference very difficult.

The known compression anastomotic rings lack the reliability of stapled anastomosis. The staple based anastomotic joining is a widely accepted practice but there is a need in improving the technology to prevent post-operative leakage of the stapled tissue seals to improve the viability of the tissue joined by staples. There is a need in an improved supporting buttress which is easy to deploy on/from existing anastomotic staplers.

SUMMARY OF THE INVENTION

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections so as to improve tissue viability, prevent tissue infection, and to prevent leakage.

The present invention, in one aspect, relates to a circular surgical stapler for anastomotic joining of tissue having a stapling head connected to an opposing anvil, with stapling head containing a plurality of deployable staples in concentric arrays. The present invention, in one embodiment, relates to a circular stapling assembly for anastomotically joining tubular tissue sections comprising: a circular anvil; a circular staple head assembly having a centrally located passage and a knife located in the passage; a moveable shaft connecting the anvil and staple head; an elongated shaft extending from the staple head assembly and gripping means; and at least one reinforcing buttress comprising a substantially flat disk of a flexible, bioabsorbable material having a centrally located aperture and a plurality of radiating slits directed from said centrally located aperture towards a periphery of said disk that forms a plurality of leaflets, said slits terminating in end apertures at a distance from said periphery.

The present invention, in another embodiment, relates to a circular anastomosis stapler kit comprising: a reinforcing buttress material comprising a substantially flat disk of a flexible, bioabsorbable material having a centrally located aperture and a plurality of radiating slits directed from said centrally located aperture towards a periphery of said disk that forms a plurality of leaflets, said slits terminating in end apertures at a distance from said periphery; an anastomotic stapler comprising a stapling head and an anvil moveable longitudinally relative to the stapling head and mounted on an axially extending moveable shaft, with the stapling head containing a plurality of deployable staples, a deployment tool comprising a hollow cylindrical body with a slidable plunger partially disposed in said body; a cylindrical radially expandable spring sized to fit within said hollow cylindrical body and within a knife cavity of said stapling head.

The present invention, in yet another embodiment, relates to a method of establishing an anastomotic joint between tubular tissue lumens with the anastomotic stapler kit comprising the steps of: axially positioning the spring in a compressed state inside the hollow cylindrical body; axially positioning the buttress between the spring inside the hollow cylindrical body and the stapling head; optionally inserting the hollow cylindrical body into a knife cavity of the stapling head thus bending the leaflets of the buttress into the knife cavity; moving the spring using the slidable plunger from the hollow cylindrical body into a knife cavity of the stapling head thus bending the leaflets of the buttress into the knife cavity; allowing the spring to radially expand in the knife cavity thus immobilizing the leaflets inside the knife cavity with said spring; removing the hollow cylindrical body; positioning the stapling head inside a first tubular tissue and positioning the anvil inside a second tubular tissue; connecting the anvil to the stapling head via the shaft; approximating the anvil and the stapling head and compressing said first and second tubular tissues and said buttress between the stapling head and the anvil; firing the anastomotic stapler and establishing the anastomotic joint between said first and second tubular tissues; severing the leaflets from the buttress.

DETAILED DESCRIPTION OF THE INVENTION

Surgery often involves joining of two or more layers of tissue together with optional simultaneous sectioning of a portion of the tissue along the staple line. For example, colorectal surgery in many cases involves the resection of a segment of the colon and rectum. Following a colorectal resection, the colon and rectum are drawn together with a circular stapler and an end-to-end anastomosis is performed. Post-op leakage of the anastomosis has been shown to lead to morbidity and mortality.

Typical surgical stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component.

Figure 1:
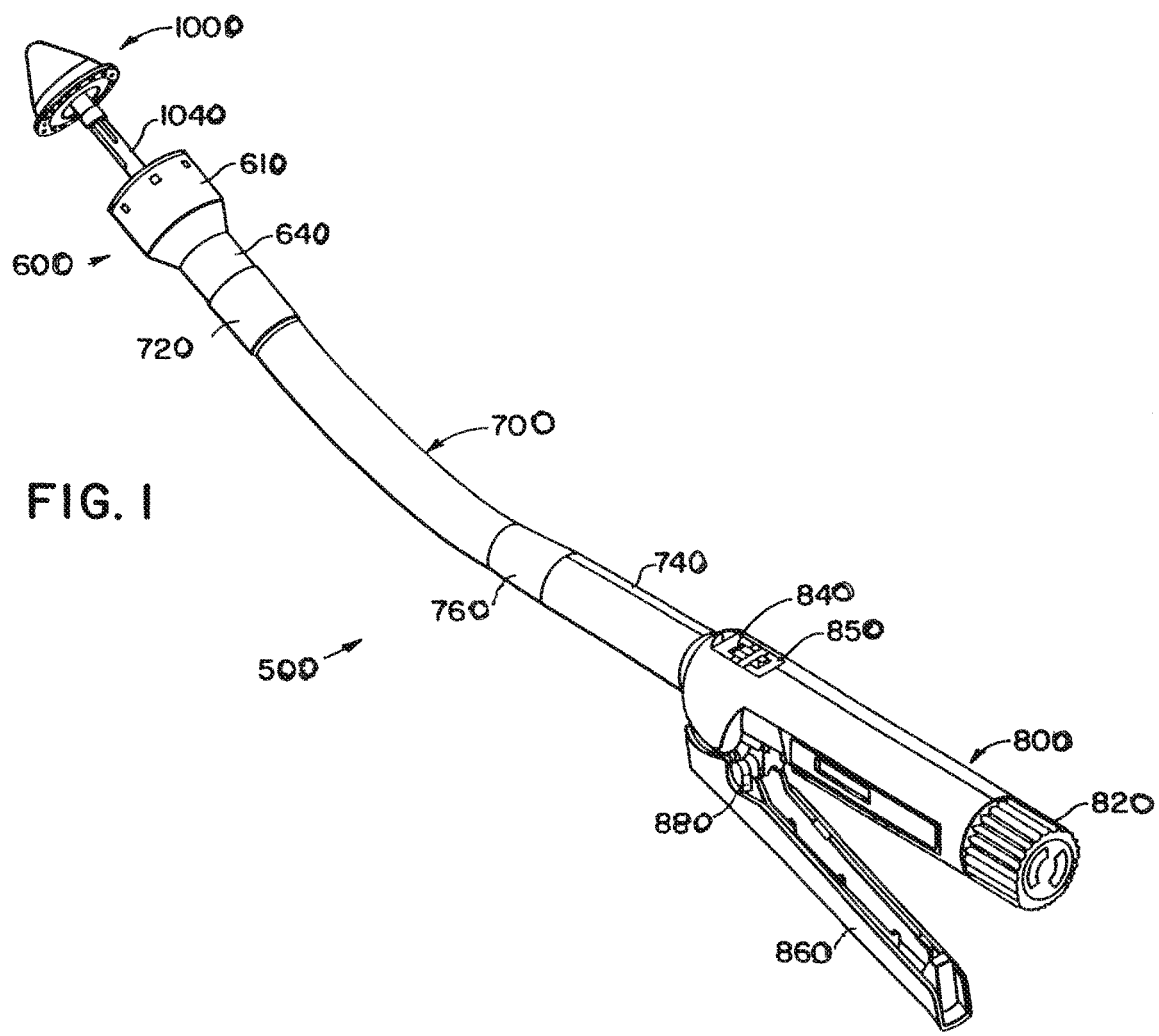
FIG. 1 shows a perspective view of a circular surgical stapling instrument.

Referring now to FIG. 1, a generic surgical anastomosis stapling instrument or stapling device for performing a circular anastomosis stapling operation is shown, with the figure taken from the U.S. Pat. No. 5,271,544 "Surgical anastomosis stapling instrument", assigned to Ethicon, Inc., Somerville, N.J., and incorporated herein by reference in its entirety for all purposes. Various modifications and iterations of the shown stapling device are known in the art, having similar features. The circular anastomosis surgical stapling instrument 500 includes a distal stapling head assembly 600 connected by a longitudinally curved support shaft assembly 700 to a proximal actuator handle assembly 800. The stapling instrument includes an anvil assembly or anvil 1000 which is slidable longitudinally relative to the stapling head assembly 600 and mounted on an axially extending moveable shaft 1040. An optional rotatable adjusting knob 820 is provided at the proximal end of the actuator handle assembly 800 for adjusting the spacing between the stapling head assembly 600 and the anvil assembly 1000. An optional movable indicator 840 is visible through an optional window 850 on top of the handle assembly 800 to indicate the staple height selected by rotation of the adjusting knob 820. The indicator 840 is movable indicating that the anvil gap is within a desired operating range of the stapling instrument 500. The position of the indicator 840 also indicates whether the selected staple height is large or small.

A staple actuating lever 860 is pivotally mounted on the actuator handle assembly 800 for driving the surgical staples from the stapling head assembly 600 when the anvil assembly 1000 is closed to provide the desired staple height. A pivotal latching member 880 is mounted on the handle assembly 800 for locking the staple actuating lever 860 against movement to preclude actuation of the stapling head assembly 600 when the anvil gap is outside of a predetermined range. The stapling head assembly 600 includes a tubular casing 610 as well as a hollow tubular connector 640 at the proximal end of the casing 610 which receives the distal end of the support shaft 700. A ferrule or sleeve 720 overlaps the joint between the tubular connector 640 and the distal end of the support shaft 700. The proximal end of the support shaft 700 is received by a tubular extension 740 at the distal end of the actuator handle assembly 800. A ferrule or sleeve 760 overlaps the joint between the proximal end of the support shaft 700 and the distal end of the tubular extension 740. The movable indicator 840 is visible through a window 850 on top of the handle assembly 800 to indicate the staple height selected by rotation of the adjusting knob 820.

Other versions and modifications of the circular surgical stapler are known to a skilled artisan. There are typically at least two and frequently more concentric stapling lines or concentric circular rows of staples-containing slots surrounding shaft 1040, with staples in each row typically staggered or offset relative to the staples in the adjacent row, to improve the sealing and prevent leakage along the stapling line.

Clinical evidence shows the formation of a full wall intestinal defect at or near the anastomotic site may occur as soon as 1-2 days post-op, with typical time period when the clinical symptoms of leaks occur being from 1 to 5 days post-op. See, for example, K. Jonsson, H. Jiborn, B. Zederfeldt, "Breaking strength of small intestinal anastomoses", The American Journal of Surgery, v. 145, pp. 800-803, 1983; Y.-H. Ho, M. A. T. Ashour, "Techniques for colorectal anastomosis", World Journal of Gastroenterology, 16(13), pp. 1610-1621, 2010.

According to the present invention, there is provided a reinforcing buttress and devices and methods to deploy such reinforcing buttress, with the reinforcing buttress attached by the staples from a circular anastomotic stapler during establishment of the anastomotic joint connecting two parts of a tissue lumen.

Figure 2A:
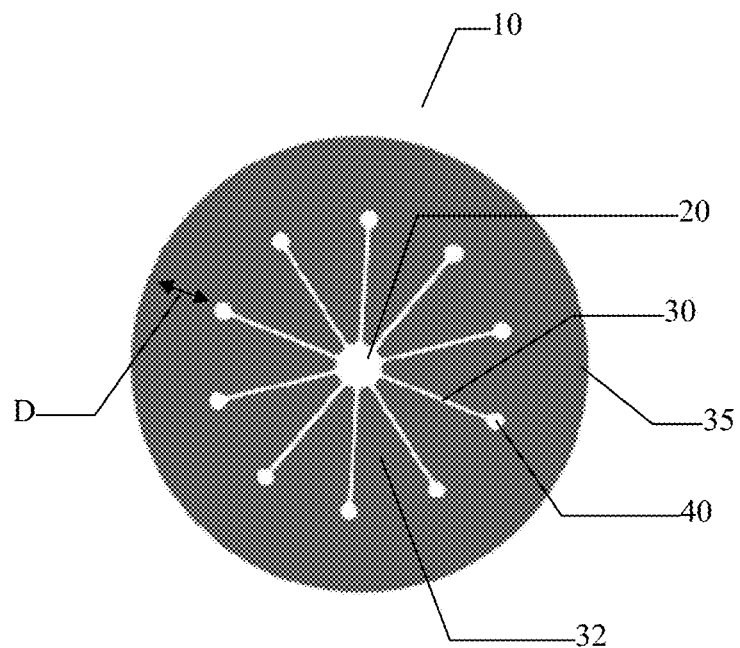
FIGS. 2A and 2B show schematic top views of the reinforcing buttress.

Referring now to FIG. 2A, a schematic top view of one embodiment of a reinforcing buttress 10 of the present invention is shown. Buttress 10 comprises a substantially flat disk, having a round centrally located aperture 20 and a plurality of radial slits 30 which start from an edge of aperture 20 and extend radially towards a peripheral edge of buttress 10 but not reaching external circumference 35 of buttress 10. Radial slits 30 terminate at a distance D from external circumference 35. Distance D corresponds to area being stapled by the anastomotic stapler and is at least equivalent to the width of staple lines (not shown). Distance D further corresponds distance between stapling head outside circumference and circular knife. Radial slits 30 form triangularly shaped leaflets or segments or flaps 32 which are used for attaching buttress 10 to stapler head 600 and anvil 1000. Triangular flaps 32 can be bent out of plane of buttress 10 by exerting force on triangular flaps 32. Radial slits 30 terminate in stress relieving end apertures 40 which prevent cracking of buttress 10 material when triangular flaps 32 are bent out of plane of buttress 10. Radial slits 30 can be preferably evenly spaced apart.

Figure 2B:
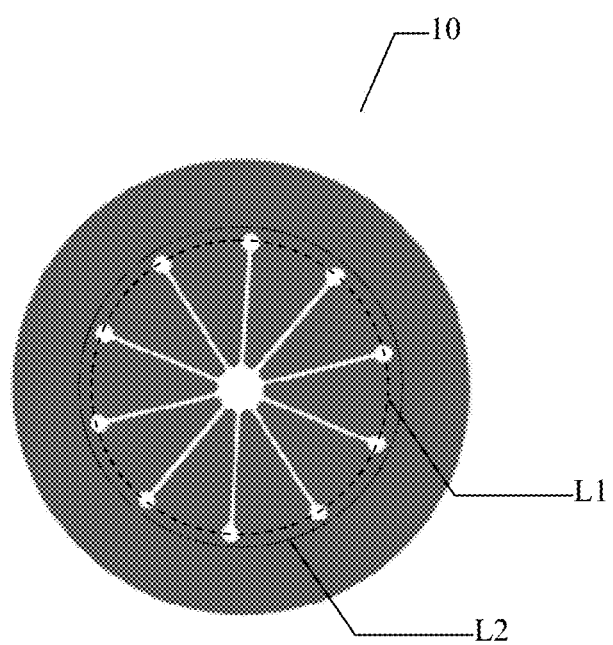

Referring to now FIG. 2B, severing of central portion of buttress 10, i.e. of leaflets 32 by the circular knife can be made at the end of radial slits 30 or at the stress relieving end apertures 40, as schematically shown by dashed line L1. Alternatively, severing of central portion of buttress 10, i.e. of leaflets 32 by the circular knife can be made between the end of radial slits 30 or between the stress relieving end apertures 40 and external circumference 35 of buttress 10, but proximal to the end of radial slits 30 or stress relieving end apertures 40, as schematically shown by dotted line L2.

Figure 3A:
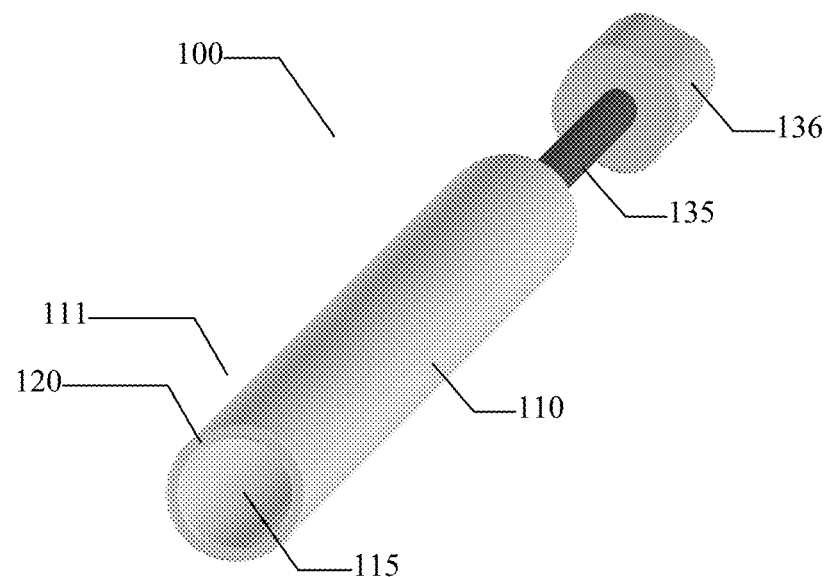
FIGS. 3A and 3B show schematic perspective views of the buttress deployment tool.
Figure 3B:
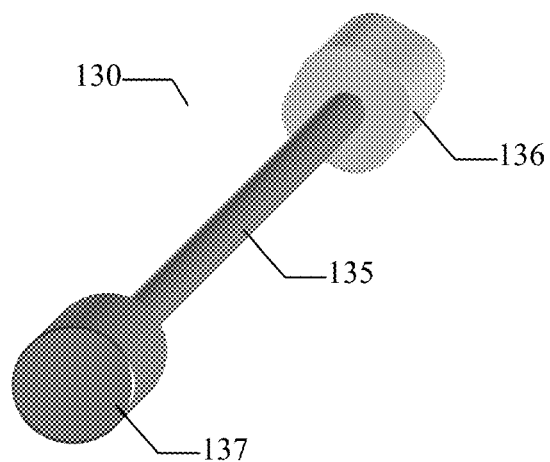

Referring now to FIGS. 3A and 3B, a schematic perspective view of a buttress deployment tool 100 is shown, with FIG. 3A showing tool 100 comprising a hollow cylindrical body 110 which has an axial cylindrical opening 115 surrounded by a wall 120. Plunger 135 is partially disposed in cylindrical opening 115, with plunger 135 comprising, as also shown in FIG. 3B, stem 135 on distal end of which is positioned a piston 137. On proximal end of stem 135 is positioned handle 136. Piston 137 is positioned close to distal end 111 of deployment tool 100 and is sized to be slidably moveable within cylindrical body 110 when actuated by handle 136.

Figure 4A:
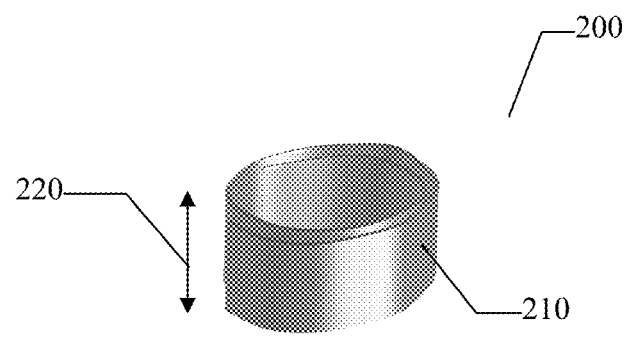
FIGS. 4A and 4B show a schematic perspective view and schematic top view of the spring.
Figure 4B:
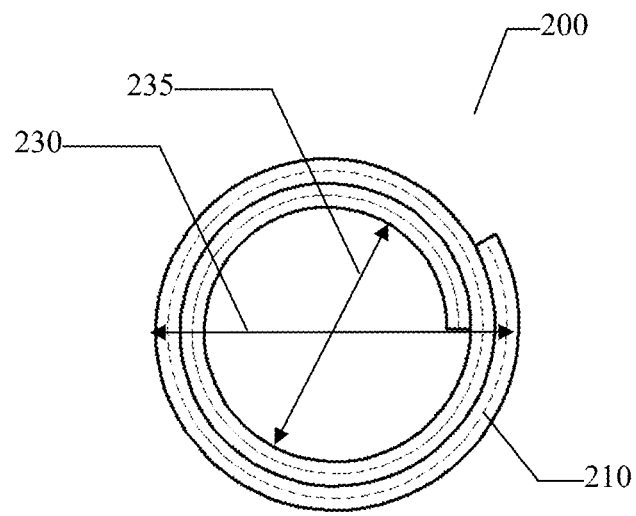

Referring now to FIG. 4A, a schematic perspective view of a spring 200 shown, with spring 200 comprising a spiral spring formed as a generally cylindrical spiral of height 220 made of a flat metallic or polymeric strip or foil 210 resulting in radially expandable resilient spiral of tightly wound into a cylinder. FIG. 4B shows schematic top view of spring 200 having external diameter 230 and internal diameter 235. Spring 200 can comprise from less than 2 full circles or turns of foil as shown in FIG. 4A, to slightly over 2 full circles, as shown in FIG. 4B, to 3-10 full circles.

Figure 5A:
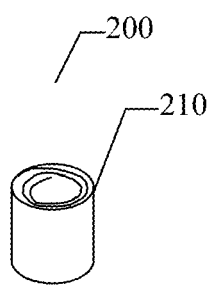
FIGS. 5A, 5B, 5C and 5D show schematic views of various embodiments of the spring.
Figure 5B:
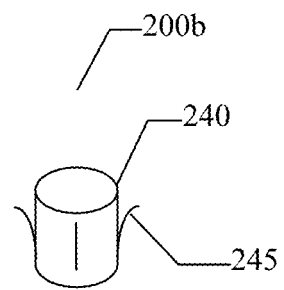
Figure 5C:
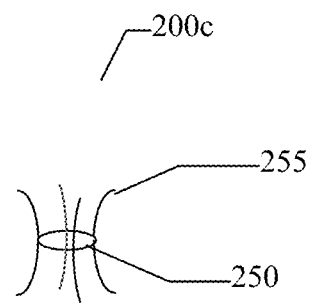
Figure 5D:
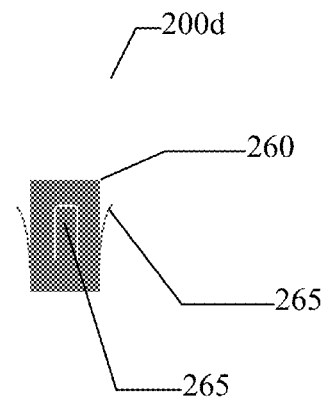

Referring now to FIGS. 5A-5D, schematic views of various embodiments of spring 200 are shown. FIG. 5A shows spring 200 as described above. FIG. 5B shows a spring 200b comprising a cylindrical body 240 with a plurality of memory-shape radially expanding arms 245. FIG. 5C shows a spring 200c comprising a round support ring 250 with a plurality of memory-shape radially expanding arms 255. FIG. 5D show a side view of a spring 200d comprising a cylindrical body 260 with a plurality of memory-shape radially expanding flaps 265. All preferred embodiments of spring 200 provide a hollow, generally cylindrical structure which can be compressed radially and then expand radially when compression is removed.

Figure 6A:
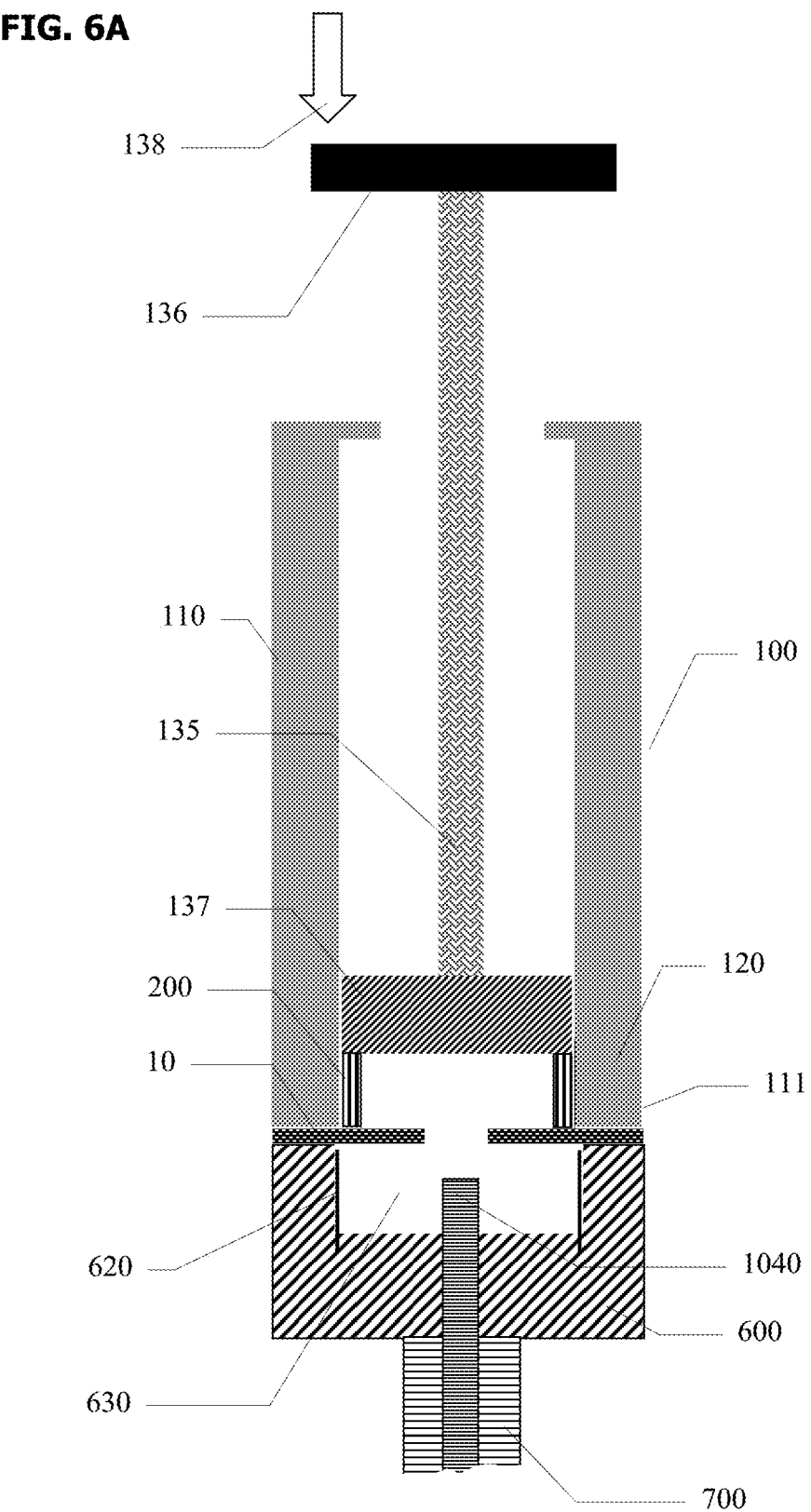
FIGS. 6A, 6B and 6C show schematic cross-sectional side views of the initial position in the use of deployment tool to deploy buttress onto stapling head.

Referring now to FIG. 6A, a schematic cross-sectional side view illustrates the use of deployment tool 100 to deploy buttress 10 onto stapling head 600. Deployment tool 100 is shown axially aligned and abutting stapling head 600, with buttress 10 positioned between and compressed by distal end 111 of deployment tool 100 and stapling head 600. Wall 120 of cylindrical body 110 is shown aligned with stapling head 600, with spring 200 positioned in the compressed state within cylindrical body 110 at distal end 111 of deployment tool 100. Stapling head is shown having circular knife 620 deployed within knife cavity 630. Deployment mechanisms for knife 630 and staple are not shown for simplification.

Figure 6B:
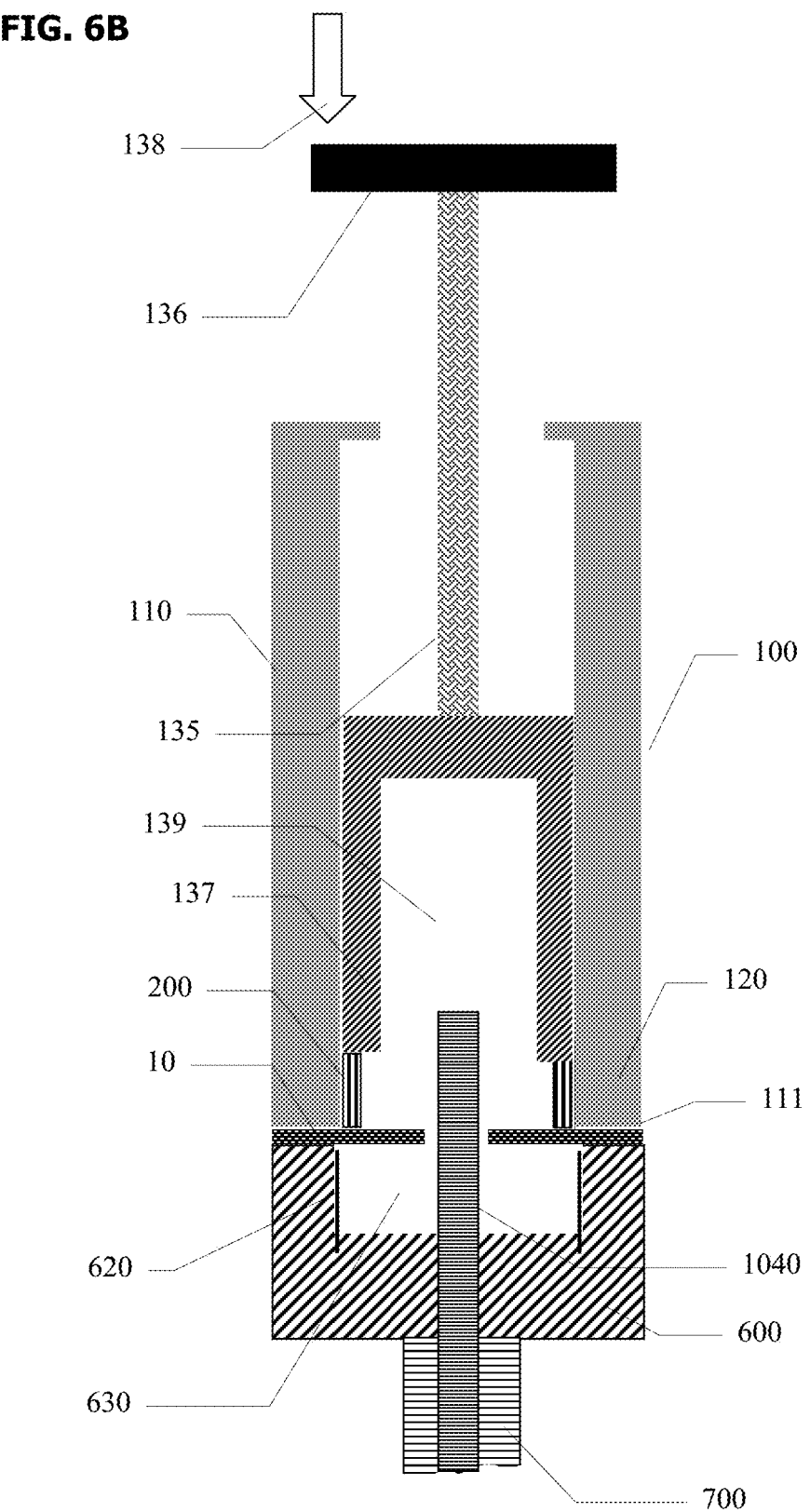
Figure 6C:
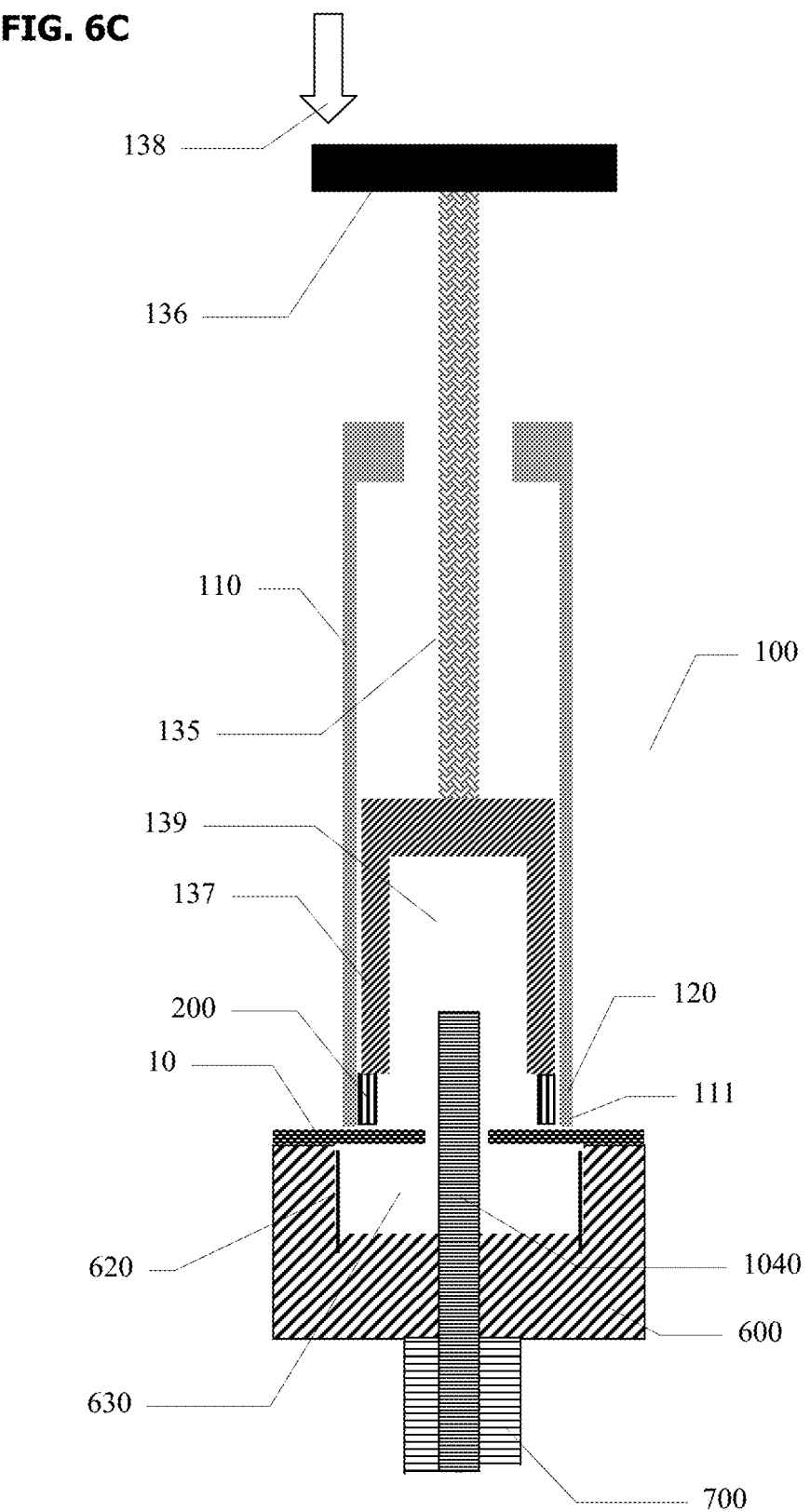

Referring now to FIG. 6B, piston 137 has an optional cavity 139 so as to more easily to accommodate shaft 1040 when shaft 1040 is in extended position i.e. protruding above stapling head 600 as shown in FIG. 6B. Referring now to FIG. 6C, a schematic cross-sectional side view illustrates an embodiment of deployment tool 100 and its use of to deploy buttress 10 onto stapling head 600. Deployment tool 100 is shown axially aligned and abutting stapling head 600, with buttress 10 positioned between and compressed by distal end 111 of deployment tool 100 and stapling head 600. Wall 120 of cylindrical body 110 is aligned with stapling head 600, with spring 200 positioned in the compressed state within cylindrical body 110 at distal end 111 of deployment tool 100. Stapling head 600 has a circular knife 620 deployed within knife cavity 630. Piston 137 having an optional cavity 139 so as to more easily to accommodate shaft 1040 when shaft 1040 is in extended position.

In the embodiment shown in FIG. 6C, the outside diameter of cylindrical body 110 is selected so that cylindrical body 110 can fit within knife cavity 630. This is different from the embodiments of FIGS. 6A, 6B, where outside diameter of cylindrical body 110 matches the outside diameter of stapling head 600. For deployment of buttress 10 onto stapling head and securement of buttress 10 with spring 200, pushing on handle 136 in the direction of arrow 138 moves stem 135 and piston 137 towards distal end 111.

Figure 7A:
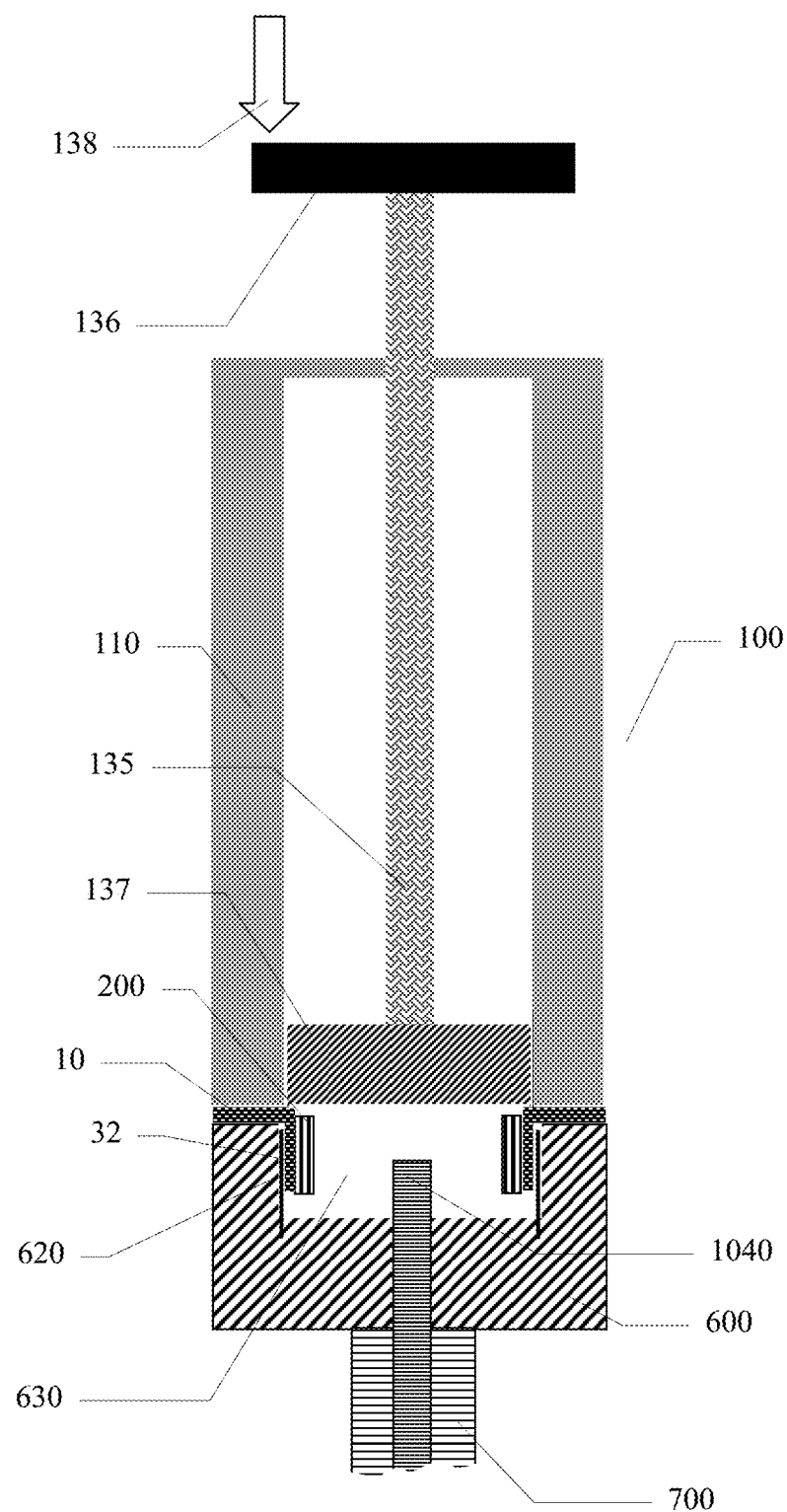
FIGS. 7A, 7B, 7C and 7D show schematic cross-sectional side views of the process of deploying buttress using the deployment tool onto stapling head.
Figure 7B:
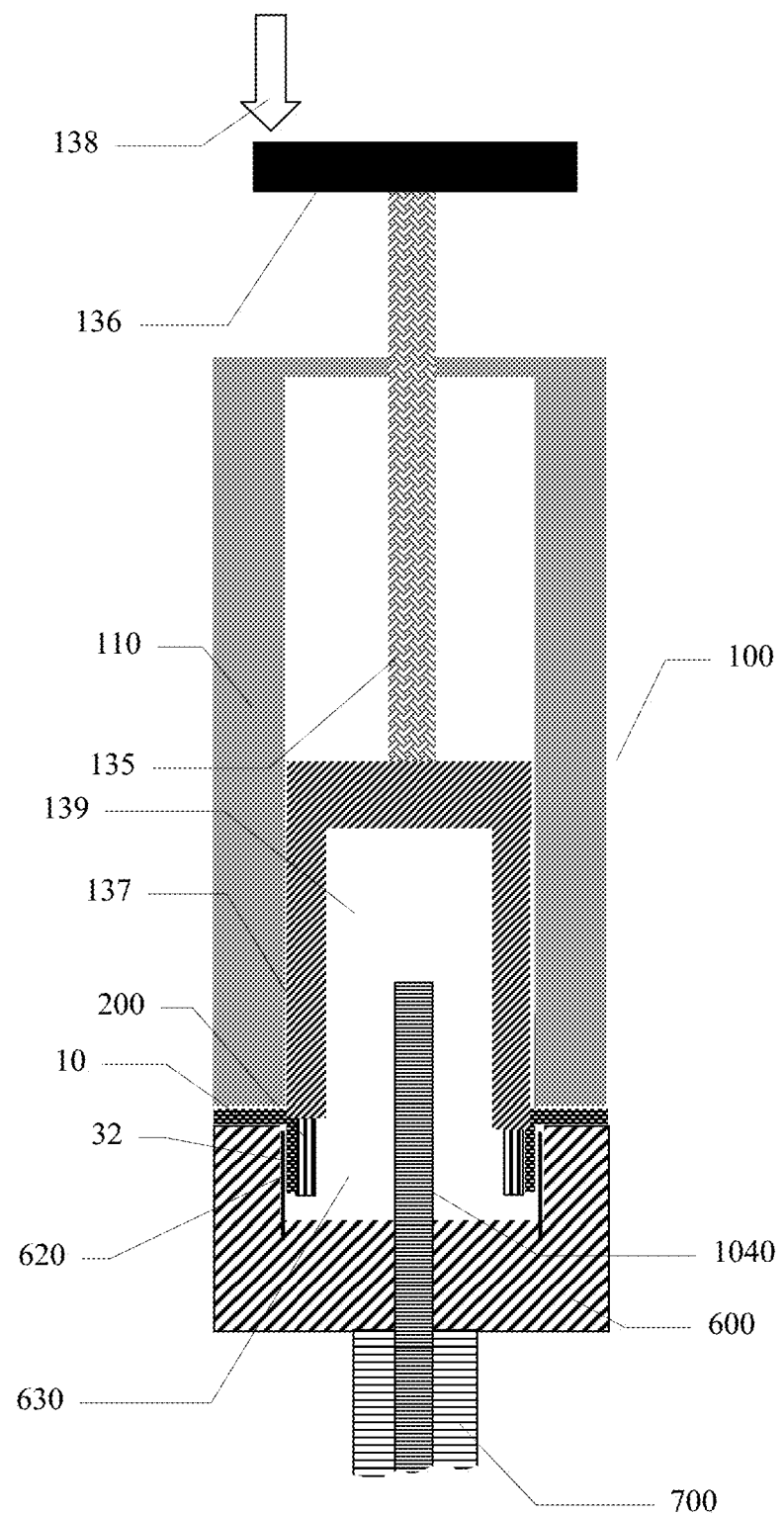

As shown in FIGS. 7A and 7B, corresponding to embodiments of FIGS. 6A and 6B, and as a result of pushing handle 136 in the direction of arrow 138, which moves stem 135 and piston 137 towards distal end 111, spring 200 is moved into knife cavity 630, bending flaps 32 into knife cavity 630. Spring 200 expands radially and presses flaps 32 against knife 620 within knife cavity 630. Thus spring 200 immobilizes buttress 10 on stapling head 600 by pressing flaps 32 and holding flaps 32 against circular knife 620.

Figure 7C:
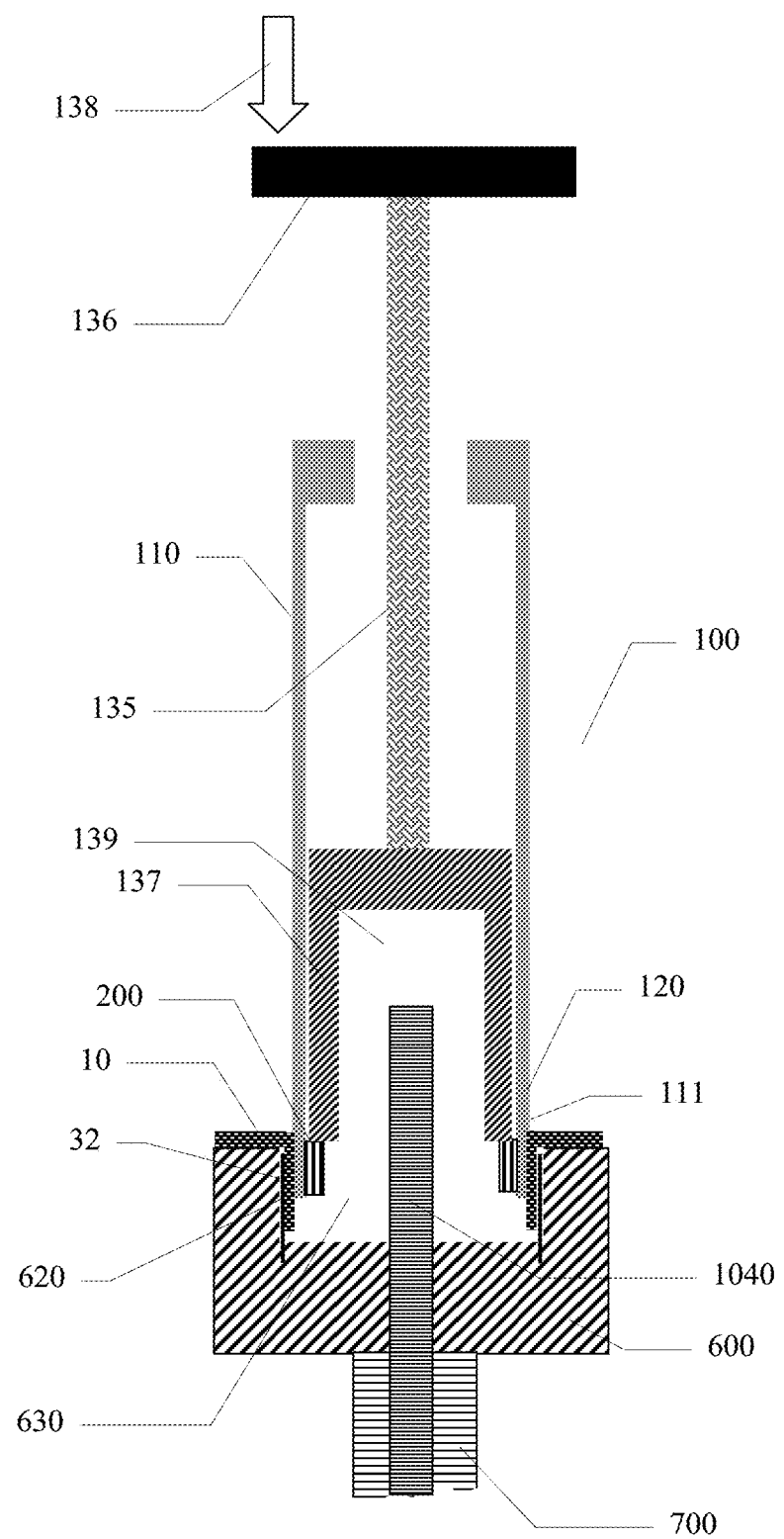
Figure 7D:
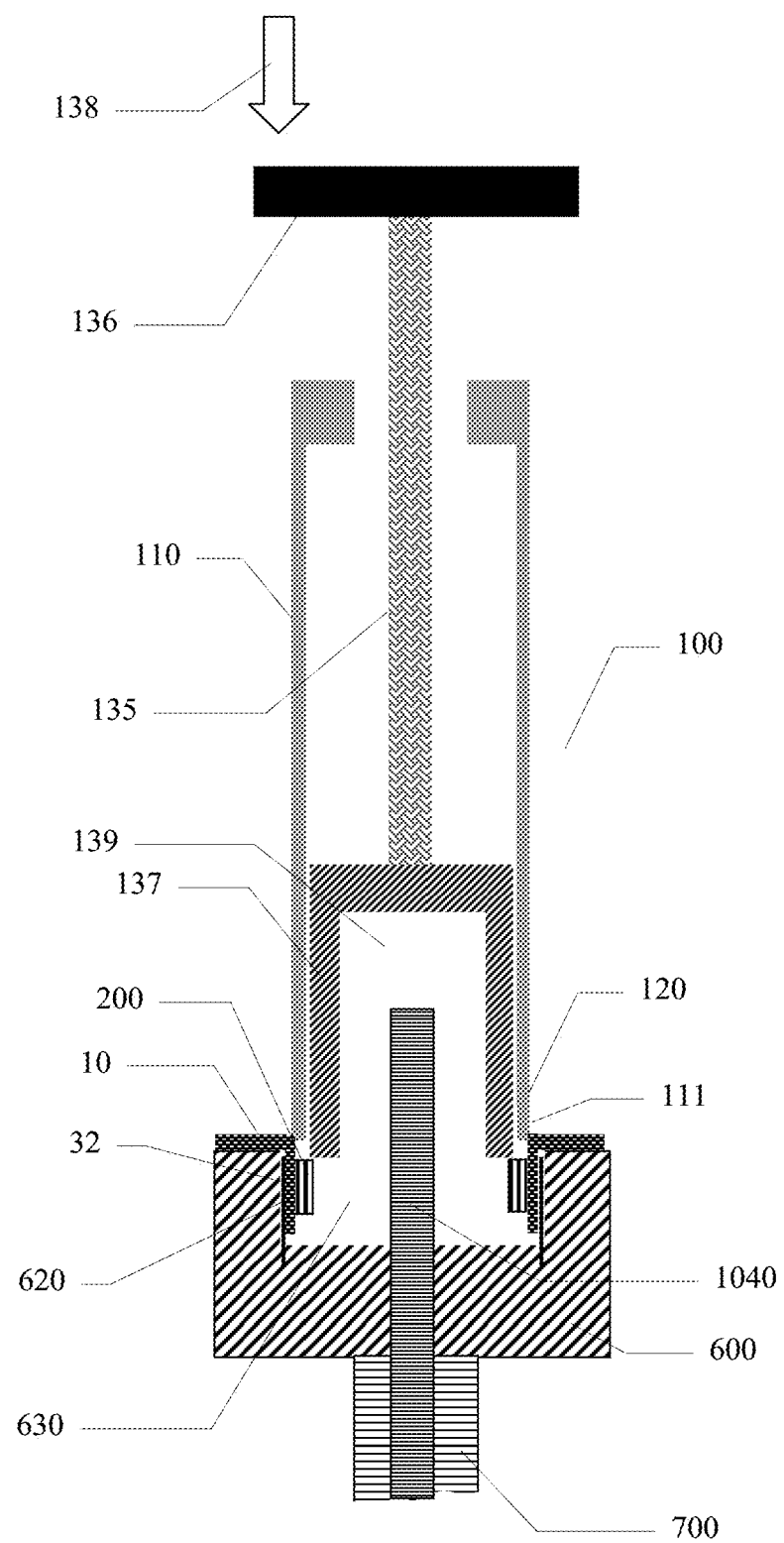
Figure 8:
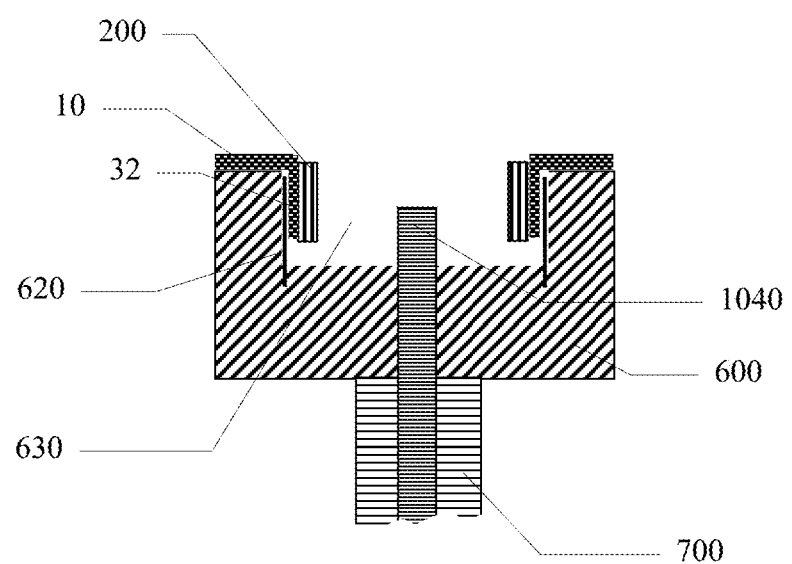
FIG. 8 shows a schematic cross-sectional side view of buttress mounted onto stapling head.

Referring now to FIGS. 7C and 7D, corresponding to embodiment of FIG. 6C, cylindrical body 110 is pushed into knife cavity 630, bending flaps 32 into knife cavity 630, resulting in schematic cross-sectional view of FIG. 7C. In the embodiments shown in FIGS. 7C and 7D, outside diameter of cylindrical body 110 is selected so that cylindrical body 110 can fit within knife cavity 630. This is different from embodiments of FIGS. 7A, 7B, where outside diameter of cylindrical body 110 is close to or matches the outside diameter of stapling head 600.

Pushing on handle 136 in the direction of arrow 138 and moving stem 135 and piston 137 towards distal end 111, spring 200 is then moved into knife cavity 630, while simultaneously withdrawing cylindrical body 110 from knife cavity 630, resulting in schematic cross-sectional view of FIG. 7D. Spring 200 expands radially and presses flaps 32 against knife 620 within knife cavity 630. Thus spring 200 immobilizes buttress 10 on stapling head 600 by pressing flaps 32 and holding flaps 32 against circular knife 620.

After immobilizing buttress 10 on stapling head 600 via spring 200 as described above, and referring to FIG. 8, showing a schematic cross-sectional side view, deployment tool 100 is removed, leaving stapling head 600 supported on shaft assembly 700 with moveable shaft 1040 visible in knife cavity 630. Buttress 10 is disposed on stapling head 600, with a portion of buttress 10 from external circumference 35 to approximately termination of radial slits 30, i.e. a portion corresponding to approximately distance D from external circumference 35 is disposed on top of stapling head 600, with flaps 32 held by spring 200 against knife 620 within knife cavity 630.

Figure 9:
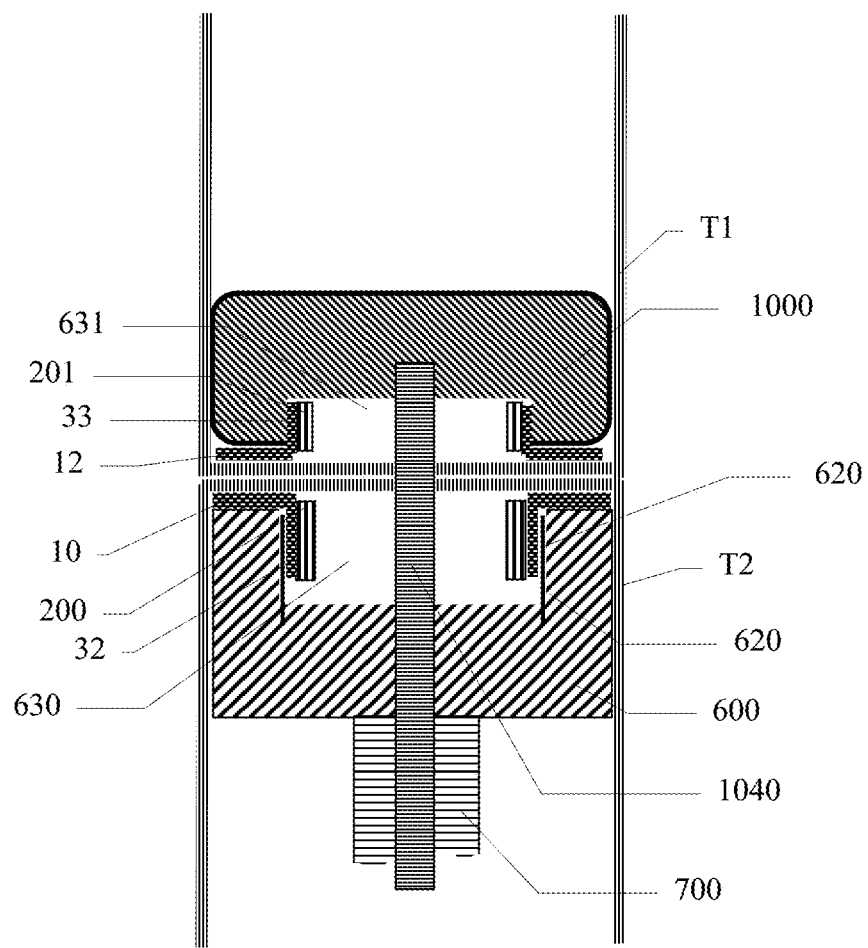
FIG. 9 shows a schematic cross-sectional partial side view of a portion of circular stapler performing anastomotic joining of tubular tissues.

Referring now to FIG. 9, a schematic cross-sectional partial view of a portion of circular stapler 500 performing anastomotic joining of tubular tissues T1 and T2 is presented. Anvil 1000 is shown disposed within tubular tissue T1 and connected to stapling head 600 via moveable shaft 1040. Stapling head assembly 600 is shown disposed within tubular tissue T2 and supported on support shaft assembly 700. For simplification, the mechanism of staples 110 deployment and mechanism of deploying tissue cutting concentric knife 620 are not shown.

Anvil 1000 is shown with an optional buttress 12, which is similar to buttress 10 described above, similarly deployed on anvil 1000 using spring 201 disposed in anvil cavity 631 and immobilizing flaps 33 in anvil cavity 631. Optional buttress 12 is deployed in a process similar to process described above for buttress 10, whereby deployment tool 100 is used to deploy optional buttress 12 onto anvil 1000. Deployment tool 100 is axially aligned and abutting anvil 1000, with optional buttress 12 positioned between and compressed by distal end 111 of deployment tool 100 and anvil 1000. Spring 201 is moved into anvil cavity 631, bending flaps 33 into anvil cavity 631. Spring 201 expands radially and presses flaps 33 against anvil cavity 631. Thus spring 201 immobilizes optional buttress 12, if installed, on anvil 1000 by pressing flaps 33 and holding flaps 33 against anvil cavity 631. Optionally, deployment tool 100 has a central axial opening (not shown) in distal end 111 of plunger 135, specifically in stem 135 and piston 137 in order to accommodate anvil pin (not shown).

FIG. 9 shows anvil 1000 and stapling head 600 approximated, compressing between them tissue T1 and T2 as well as a portion of buttress 10 and a portion of optional buttress 12 disposed inside tubular tissues T2 and T1 respectfully.

Figure 10:
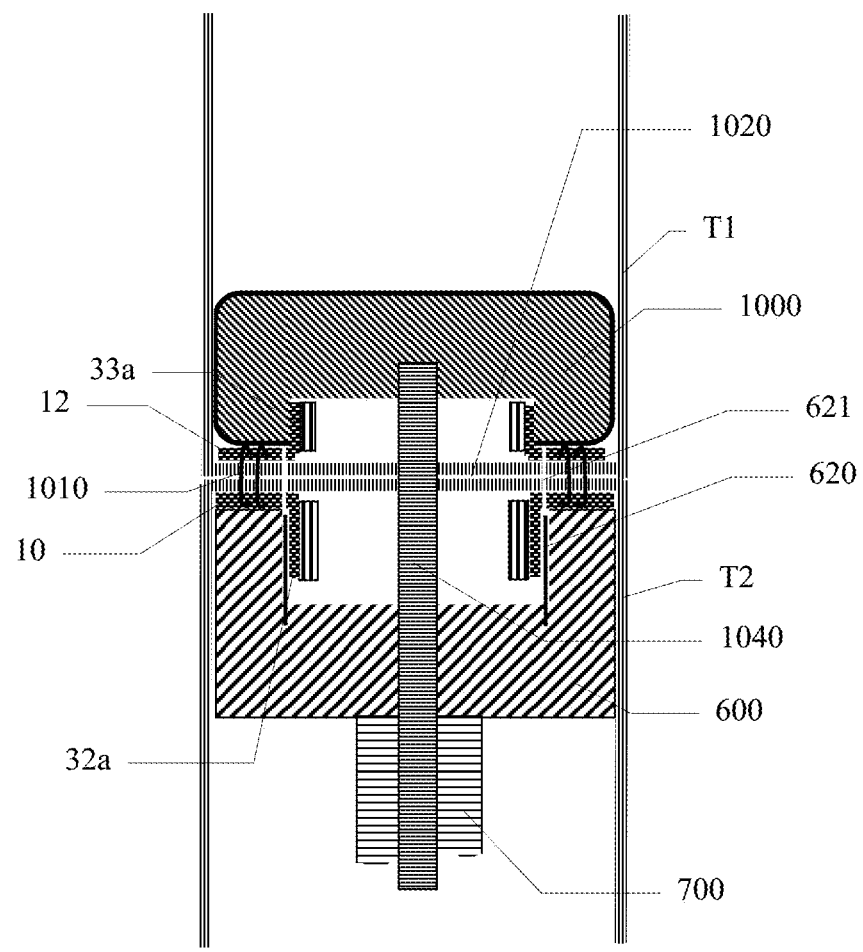
FIG. 10 shows a schematic cross-sectional partial side view of a portion of circular stapler performing anastomotic joining of tubular tissues.

Referring now to FIG. 10, a schematic cross-sectional partial view of a portion of circular stapler 500 performing anastomotic joining of tubular tissues T1 and T2 is presented with staples 1010 fired thus establishing a stapled joint between tissues T1 and T2 with staples 1010 concentrically arranged in one or more concentric rows around tissue donut or cut-out 1020. As shown, upon firing of the circular stapler 500, central portion of tubular tissues T1 and T2 is severed by circular knife 620, forming tissue cut-out 1020. At the same time staples 1010 are deployed joining tissues T1 and T2 as well as buttress 10 and optional buttress 12 to tissues T1 and T2, with buttress 10 inside tubular tissue T2 and optional buttress 12 inside tubular tissue T1. As circular knife 620 is deployed, it also severs a central portion 32a of buttress 10 approximately corresponding to flaps 32 and also severs a central portion 33a of optional buttress 12 approximately corresponding to flaps 33.

Figure 11:
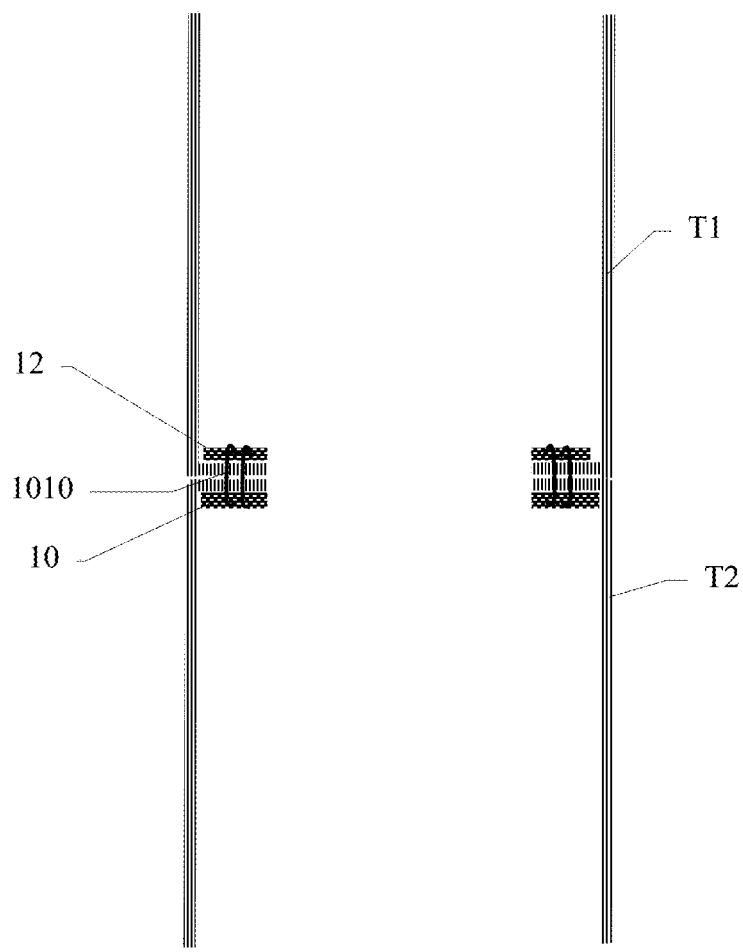
FIG. 11 shows a schematic cross-sectional side view of an anastomotic joint.

After deploying staples and cutting out tissue cutout 1020, circular stapler 500 is withdrawn. As shown in FIG. 11, this completes anastomotic joint of tissues T1 and T2 with the joint reinforced by remaining portion of buttress 10 inside tubular tissue T2 and remaining portion of optional buttress 12 inside tubular tissue T1.

Dimensions

Buttress 10 can be preferably made of absorbable materials such as natural polymers, polysaccharides, proteins, or the like, including collagen, ORC, Extra-Cellular Matrix, etc. Synthetic polymers can also be used. Buttress 10 can also be made of non-absorbable materials. Buttress 10 can also be made of composites which can include both absorbable and non-absorbable materials. Buttress 10 can also incorporate various medically useful agents, including anti-infective agents, tissue healing agents, growth factors, and the like.

The thickness of buttress 10 is from about 0.1 mm to about 3 mm, such as 0.3 mm, 0.5 mm, 1 mm, 2 mm. The diameter of buttress 10 ranges from about 10 mm to about 30 mm, such as 20 mm, 25 mm, 28 mm. Distance D is from 1 mm to 8 mm, such as 2 mm, 3 mm, 4 mm. Slits 30 are from zero to 1 mm wide such as 0.1 or 0.3 mm wide. The diameter of preferably centrally circular aperture 20 is about 2 mm to 10 mm, such as 3 mm. End apertures 40 preferably have circular diameters from about 0.2 mm to about 2 mm, such as 0.5 mm, 1 mm, 1.5 mm. The slits are preferably evenly spaced.

Spring 200 is formed of flat material, such as stainless steel metal, tightly wound into a cylinder, with metal thickness from about 0.1 mm to about 0.8 mm, such as 0.3 mm, and spring height from about 2 mm to about 10 mm, such as 5 mm. Spring 200 external diameter 230 is between 14.1 mm and 21.2 mm and internal diameter 235 is between 11.6 mm and 20.9 mm 235 (depends on metal thickness and deployment tool 100 dimensions).

Cylindrical body 110 of deployment tool 100 has cylindrical opening 115 with diameter between 14 mm to 29 mm. Cylindrical body 110 in some embodiments has external diameter substantially equal or close to stapling head diameter as shown in FIGS. 6A, 6B, 7A, 7B. In alternative embodiments, as shown in FIGS. 6C, 7C, 7D, cylindrical body 110 has external diameter selected so that cylindrical body 110 can fit within knife cavity 630. Wall 120 has thickness is from about 0.5 mm to about 4 mm, such as 1 mm, 2 mm, 3 mm.

Spring 200 external diameter 230 is sized to enable positioning of spring 200 within stapling head 600 cavity 630 as well as within cylindrical opening 115 or inside cylindrical body 110 in a compressed form.

The inventors have surprisingly discovered that the presence of end apertures 40 improved performance and prevented damage to buttress 10 during deployment, preventing propagation of cracks in the buttress.

Buttress 10 had the following dimensions: diameter 25 mm and 0.25 mm thick made of multilayer extra cellular matrix (ECM) derived from porcine soft tissue having 8 flaps 32 formed by 8 slits having distance D=4 mm, Slits 30 length of 6 mm, aperture 20 diameter 3 mm, end apertures 40 of diameter 1.2 mm. Comparative buttress was identical but had no end apertures 40.

Spring 200 was made of stainless steel film having 0.5 inch width, 4.4 inch length, 0.006 inch thickness and turned 2.5 times.

Deployment tool 100 was used to deploy buttress lo onto stapling head 600.

The inventors have discovered that buttress 10 having end apertures 40 did not exhibit any cracks (before and after stapling), while comparative buttress was identical but had no end apertures 40, showed cracks that propagated from the connection point between the leaflets into the stapled surface (distance D in FIG. 2) and therefore failed.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A method of establishing an anastomotic joint between tubular tissue lumens with a circular anastomotic stapler kit, said kit comprising:
   1) a reinforcing buttress material comprising a substantially flat disk of a flexible, bioabsorbable material having a centrally located aperture and a plurality of radiating slits directed from said centrally located aperture towards a periphery of said disk that forms a plurality of leaflets, said slits terminating in end apertures at a distance from said periphery;
   2) an anastomotic stapler comprising a stapling head and an anvil moveable longitudinally relative to the stapling head and mounted on an axially extending moveable shaft, with the stapling head containing a plurality of deployable staples,
3) a deployment tool comprising a hollow cylindrical body with a slidable plunger partially disposed in said body;
4) a cylindrical radially expandable spring sized to fit within said hollow cylindrical body and within a knife cavity of said stapling head, said spring positioned inside the hollow cylindrical body in a compressed state, said method comprising the steps of:
a) Axially positioning the spring in a compressed state inside the hollow cylindrical body;
b) Axially positioning the buttress material between the spring inside the hollow cylindrical body and the stapling head;
c) Optionally inserting the hollow cylindrical body into a knife cavity of the stapling head thus bending the leaflets of the buttress material into the knife cavity;
d) Moving the spring using the slidable plunger from the hollow cylindrical body into a knife cavity of the stapling head thus bending the leaflets of the buttress material into the knife cavity;
e) Allowing the spring to radially expand in the knife cavity thus immobilizing the leaflets inside the knife cavity with said spring;
f) Removing the hollow cylindrical body;
g) Positioning the stapling head inside a first tubular tissue and positioning the anvil inside a second tubular tissue;
h) Connecting the anvil to the stapling head via the shaft;
i) Approximating the anvil and the stapling head and compressing said first and second tubular tissues and said buttress material between the stapling head and the anvil;
j) Firing the anastomotic stapler and establishing the anastomotic joint between said first and second tubular tissues;
k) Severing the leaflets from the buttress material.

2. The method of claim 1, wherein said spring comprises a spiral made of a flat metallic or polymeric strip or foil tightly wound into a cylinder shape.

3. The method of claim 2, wherein said spring has a height from 1 mm to 5 mm.

* * * * *